(12) United States Patent
Ritter

(10) Patent No.: US 8,712,501 B2
(45) Date of Patent: Apr. 29, 2014

(54) METHOD AND DEVICE FOR SURFACE SCANNING OF A PATIENT

(75) Inventor: Dieter Ritter, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 1811 days.

(21) Appl. No.: 11/982,589

(22) Filed: Nov. 2, 2007

(65) Prior Publication Data

US 2008/0108892 A1    May 8, 2008

(30) Foreign Application Priority Data

Nov. 8, 2006    (DE) .......................... 10 2006 052 711

(51) Int. Cl.
| | | |
|---|---|---|
| *A61B 5/055* | (2006.01) | |
| *A61B 5/00* | (2006.01) | |
| A61B 5/107 | (2006.01) | |
| G01R 33/20 | (2006.01) | |
| G01R 33/34 | (2006.01) | |
| G01R 33/44 | (2006.01) | |
| G01R 33/385 | (2006.01) | |

(52) U.S. Cl.
CPC .............. *A61B 5/0064* (2013.01); *A61B 5/055* (2013.01); *A61B 5/0059* (2013.01); *A61B 5/0062* (2013.01); *A61B 5/0046* (2013.01); *A61B 5/0077* (2013.01); *A61B 5/0555* (2013.01); *A61B 5/107* (2013.01); *A61B 5/1077* (2013.01); *A61B 5/1079* (2013.01); *G01R 33/20* (2013.01); *G01R 33/34* (2013.01); *G01R 33/44* (2013.01); *G01R 33/385* (2013.01)
USPC .............................................. 600/415; 356/3

(58) Field of Classification Search
CPC .... A61B 5/0046; A61B 5/055; A61B 5/0059; A61B 5/0062; A61B 5/0064; A61B 5/0077; A61B 5/0555; A61B 5/107; A61B 5/1077; A61B 5/1079; G01R 33/20; G01R 33/34; G01R 33/44; G01R 33/385
USPC ............................... 600/407, 415; 356/3, 317
See application file for complete search history.

(56) References Cited

U.S. PATENT DOCUMENTS

| | | | |
|---|---|---|---|
| 4,679,076 | A | 7/1987 | Vikterlöf et al. |
| 5,999,840 | A | 12/1999 | Grimson et al. |
| 7,199,385 | B2 | 4/2007 | Wehrle et al. |
| 2004/0002641 | A1 | 1/2004 | Sjogren et al. |
| 2004/0144934 | A1 | 7/2004 | Wehrle et al. |

FOREIGN PATENT DOCUMENTS

| | | |
|---|---|---|
| DE | 19712844 A1 | 10/1998 |
| DE | 10260201 A1 | 7/2004 |
| JP | 61073025 A | 4/1986 |

*Primary Examiner* — Michael Rozanski

(57) ABSTRACT

The invention relates to a method for the surface scanning of a patient, arranged on a patient's couch of a medical diagnostic device, with the following steps: Radiation of a light beam from a positioning light source onto the patient, detection of the light beam on the patient by an image sensor, arranged offset relative to the light beam, with the said light beam running from the positioning light source to the patient, movement of the patient relative to the positioning light source so that the light beam passes over the body of the patient, and determination of the surface of the patient from the detected light beam. A corresponding device is also claimed.

17 Claims, 3 Drawing Sheets

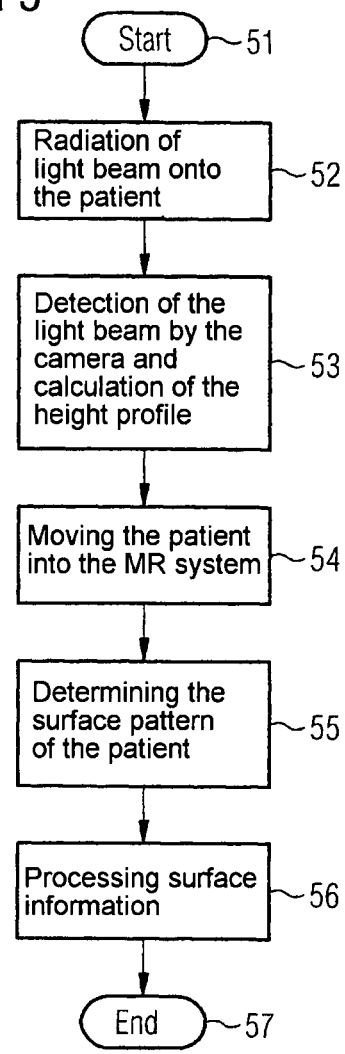

METHOD AND DEVICE FOR SURFACE SCANNING OF A PATIENT

CROSS REFERENCE TO RELATED APPLICATIONS

This application claims priority of German application No. 10 2006 052 711.9 filed Nov. 8, 2006, which is incorporated by reference herein in its entirety.

FIELD OF THE INVENTION

This invention refers to a method for surface scanning of a patient and a device for performing the method. The invention is used particularly with magnetic resonance (MR) systems, whereby the patient or patients lying on a patient's couch is/are moved into the magnet of the MR system. The invention also relates to a corresponding device.

BACKGROUND OF THE INVENTION

In the prior art, methods for scanning the surface of objects are known which can in principle be divided into two different classes. The first are passive methods such as stereo, shading or contour methods. With these passive methods, at least one camera scans the 3D contours of the object under examination. A further class of such 3D sensors for surface scanning operates according to an active method, for example with a laser scanner, the Moiré method, coherence radar method or transit time method. With active methods, coded light is radiated onto the object and the resulting pattern is evaluated. Passive methods are usually technically simpler to implement, whereas active methods, i.e. methods with active lighting, have a greater accuracy and are more robust with respect to incorrect interpretation. Both methods have their particular disadvantages, whereby on the one hand it can be difficult to position the sensors used around the object to be scanned and on the other hand the number and alignment of the cameras used and their calibration and synchronization also have to be taken into account.

SUMMARY OF THE INVENTION

The object of this invention is to obtain, in a simple and cost-effective manner, information regarding the surface characteristics of the patient by means of a medical diagnostic device such as an MR system.

This object is achieved by the features of the independent claims. Preferred embodiments of the invention are given in the dependent claims of the invention.

According to a first aspect of the invention, a method is provided for the surface scanning of a patient, with the patient being arranged on a patient's couch of a medical diagnostic device. In one step of the inventive method, a light beam from a positioning light source is directed onto the patient. Furthermore, this light beam projected onto the patient is received by an image sensor arranged offset relative to the light beam which runs from the positioning light source to the patient. In a further step, the patient is moved relative to the positioning light source so that the light beam passes over the body of the patient. The surface pattern or contour of the patient can now be determined from the course of the light beam over the body of the patient.

According to a further aspect of the invention, a device for surface scanning of the patient in the medical diagnostic device is provided, with the device having a positioning light source that radiates a light beam onto the patient. The device also has an image sensor arranged offset relative to the light beam that runs from the positioning light source to the patient. This image sensor captures the light beam projected onto the patient. Furthermore, a device is provided which moves the patient relative to the positioning light source. A computing unit can then calculate a surface pattern of the patient from the positions of the light beam detected by the image sensor. The inventive device or inventive method have the advantage that the surface of the patient can be determined in a relatively simple manner. It is necessary only to provide, in addition to the already existing devices, an image sensor such as a digital camera (CCD camera or CMOS camera) that records and evaluates the light beam projected onto the patient at an angle $\alpha$ relative to the light beam. Such image sensors are relatively inexpensive, so that just by means of the additional camera as an image sensor and the necessary evaluation software a surface pattern of the patient can be determined, which, as explained in detail in the following, can be used for several applications.

According to an embodiment of the invention, the positioning light source can be arranged in such a way that the light source runs essentially transverse relative to the direction of movement of the patient. A different course of the light beam is, of course, also possible. All that is important is that the largest possible area of the body under examination is passed over by the light beam during the movement of the patient. For example, the light source can be a laser unit such as is normally used in MR systems to determine the positioning of the patient relative to the MR system. Such laser units can, by using suitable optics, generate a light beam that passes over the patient.

If the medical diagnostic device is an MR system, the laser unit as a positioning light source is usually located at the entry of the magnet into which the patient is moved in order to reach the midpoint of the magnetic field. It is also possible to cover a larger area by using two laser units, arranged for example at the sides of the entry into the MR magnet that then generate the light beam.

According to one aspect of the invention, the height profile of the patient relative to the patient's couch is determined along the light beam. If the patient on the couch is moved in the direction of the MR magnet, a height profile of the light beam results along a direction vertical to the direction of movement. The height profile relative to the patient's couch can now be determined for several light points along the light beam, or for the complete light beam, in that with a relative person height h the offset d relative to the object height 0 in the image data of the image sensor is determined, as seen from the image sensor. In other words, the shift d of the laser beam on the two-dimensional image data of the image sensor relative to the starting position is determined, with the starting position being the light beam on the patient's couch.

From the calculated surface data of the patient and the associated positions of the patient's couch, the orientation of the patient in the diagnostic device can then be determined. This orientation of the patient can be compared with the person orientation usually entered by the operator of the diagnostic device. By means of this comparison, errors, for example a right-left confusion, when the position is entered by the operator can be reduced. From the surface scan it can be determined whether the patient was initially moved into the diagnostic device with the head in the prone or supine position or in the right or left side position. If the person was moved in feet first into the diagnostic device, it can also be checked whether the person is in the prone position, supine position or right or left side position. If the orientation of the patient determined from the surface data does not agree with that entered by the operator, a warning message can be output to the operator and/or the input patient's position can be determined using the surface data.

It is also possible to estimate the volume of the patient from the acquired surface area of the patient and the known data of the patient's couch and therefore obtain a measure for a weight of the patient. The obtained weight can then be compared with the weight input by the operator and checked for plausibility. The correct input of the weight is significant particularly with MR systems from the point of view of the SAR determination, because the upper limit of the HF power radiated into the body is determined relative to the weight of the patient.

It is also possible using the ascertained surface data to check the positioning of the patient on the patient's couch relative to the diagnostic device. For example, using the volume data it possible to predict whether a patient who is perhaps overweight or not centrally positioned will touch the inside wall of the tunnel of the diagnostic device. This information is significant in order to avoid any local burning of the patient at the contact point, which could result due to generated induction loops.

The surface data can also be used to check whether certain high frequency coils of MR systems are present and the position at which they are arranged. The correct positioning of receiving or transmitting coils can be determined from the surface pattern because the coil geometry is known per se and can be detected in the surface pattern.

Furthermore, it is possible to use the acquired surface data to determine whether the patient is fitted with an alarm transmitter by means of which the patient can trigger an alarm in an emergency. In the case of an MR system, this is usually an alarm ball, connected by an air hose and within reach of the patient, which the patient can press if necessary and thus trigger an alarm.

In a further embodiment of the invention, the 3D data record can be used to extract biometric features of the patient and thus identify, or confirm the identity of, the patient. The pattern of the surface of the patient's face is particularly suitable for this purpose.

BRIEF DESCRIPTION OF THE DRAWINGS

The invention is explained in more detail in the following with reference to the accompanying drawings. The drawings are as follows.

DETAILED DESCRIPTION OF THE INVENTION

Figure 1:
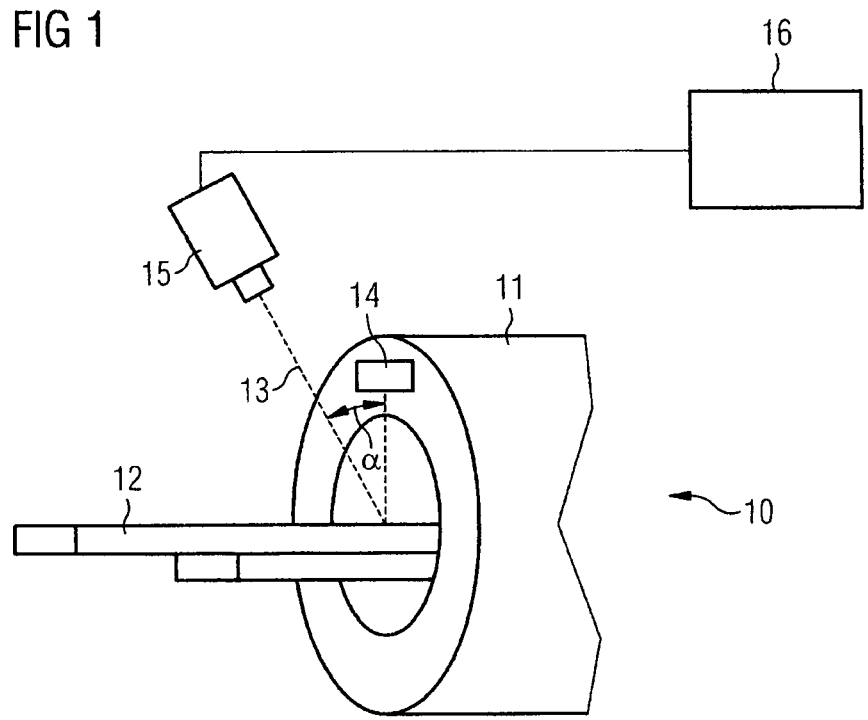
FIG. 1 A schematic of the inventive device for determining the surface pattern in an MR system, FIG. 2 Example of the height profile of a light beam when a patient crosses the light beam, FIG. 3 The height profile of FIG. 2 detected by the image sensor, FIG. 4 A sketch showing the calculation of the height profile using the offset d, and FIG. 5 A schematic of a flow diagram for establishing the surface pattern of a patient.
Figure 1:
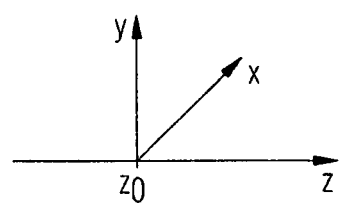

FIG. 1 shows a schematic of an MR system 10. This MR system has a magnet 11 for generating a basic magnetic field B0. To generate MR images of a patient (not shown in FIG. 1), the patient is moved on a patient's couch 12 along the Z access through an opening 13 of the magnet 11. A magnetic resonance system of this kind has a positioning light source 14 in the form of a laser that is used to determine the position of the patient and of the existing detection coils relative to the system of coordinates of the MR system.

According to the invention, the MR system 10 also has an image sensor 15 in the form of a CCD camera that can generate two-dimensional image data. Furthermore, an evaluation and computing unit 16 is provided that can create a surface pattern or three-dimensional data record of the patient from the received image data. The image sensor is arranged at an angle $\alpha$ relative to the light beam, which runs from the positioning light source to the couch 12. The angle $\alpha$ can for example be between 10° and 40°.

Figure 2:
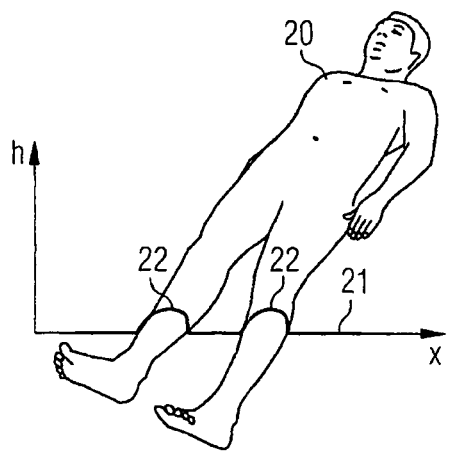

The way in which a three-dimensional layer profile of the patient can be obtained in a simple manner using the system shown in FIG. 1 is explained in the following in conjunction with FIGS. 2, 3 and 4. The laser 14 radiates a light beam, which is essentially vertical to the direction of movement z of the couch 12, onto the patient's couch on which the patient is moved into the magnet. The height profile h(x) at position $z_0$ is shown in FIG. 2. If no patient is present, the light beam lies on the patient's couch at the height 0. If a patient is moved along the z-axis into the magnet, the height profile h changes, as shown for example in FIG. 2, when the light beam falls on the patient. This shift of the light beam is now recorded at an angle $\alpha$ by the CCD camera 15. In this case, the camera detects a shift d of the laser beam relative to the starting position. From the shift determined from the image, d(x) can then be calculated using geometric features of the height profile h(x), as explained later in conjunction with FIG. 4. When the patient 20, shown in FIG. 2, is moved in, a profile pattern 21 with two maxima 22 results, for example due to the two legs. This real object height h is detected by the camera as a pattern d(x), which is designated by the reference character 31. This shift d of the laser beam is detected by the camera, with both maxima 32 now depending on the angle of the camera position relative to the light source.

Figure 4:
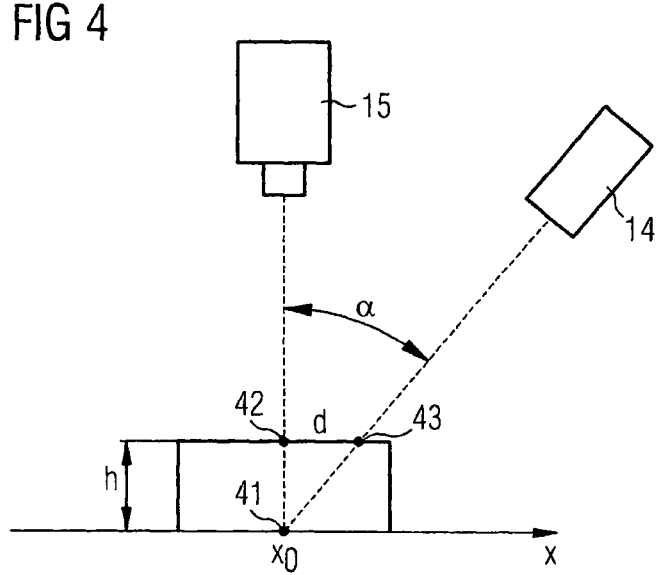

FIG. 4 shows this geometric relationship between the object height h and the offset d in more detail. For better understanding, the camera 15 is arranged vertical relative to the patient in the example from FIG. 4, whereas the laser unit 14 is arranged offset up to an angle $\alpha$. An arrangement as shown in FIG. 1 is, of course, also possible. If there is no patient on the couch, the light point 41 of the laser lies at $x_0$. If a patient with a height h is now moved into the light beam, the light point lies at point 43. The camera 15 detects the body with the height h as an offset of the light point along the x axis about d. This real height profile of the patient is detected by the camera in such a way that the point lying at $x_0$ now has an offset d relative to the object height 0. The camera detects the light point at point 43. As can be easily seen in FIG. 4, the relationship between the angle $\alpha$ and the object height h and also the offset d is as follows: tan $\alpha$=d/h. If the angle $\alpha$ at which the camera is arranged relative to the laser unit is known, the real height in the pattern h(x) and therefore the surface pattern or the volume of the patient 20 can be obtained by the determination of the profile pattern d(x).

FIG. 5 is a schematic showing the steps necessary to calculate a 3D data record of the patient. After a start in step 51, the light beam is radiated onto the patient in step 52. In step 53 the light beam is then detected by the camera. It is important for determining the surface profile that the camera is not arranged parallel to the light beam that radiates from the laser unit onto the patient. It is not possible in such a case to detect the height profile. It makes no difference in this case whether the laser radiates vertically onto the patient as shown in FIG. 1, with the camera being arranged at an angle to it, or the arrangement is vice versa as shown in FIG. 4. Equally, two laser units that generate the light beam can also be provided.

Figure 3:
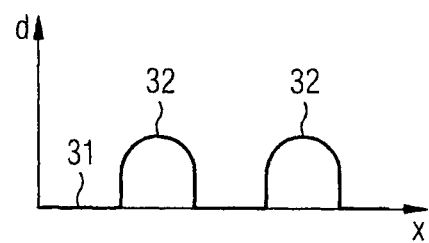

During the radiation of the light beam and the detection by the camera, the patient is moved into the MR system by moving the patient's couch, so that the surface profile of the patient can be determined by continuously recording image date while the patient is being moved in, as was described in conjunction with FIGS. 2-4. To determine 3D data record, the light beam in this case can be divided into individual points and the distance of the points from the zero line can be determined for various z values. From the surface information determined in step 55, various applications or processes are then possible in step 56. An example of an application is a check in 56 to determine whether the patient's position as determined by the camera agrees with the position input by the operator. Furthermore, a check of the weight details determined from the patient's volume is possible. As an alternative or addition, a check can also be carried out to determine whether the necessary local coils are placed at the correct patient positions. For example, the presence of the neck coil can be checked or the correct position of the knee coil. The height of the coil at the leg and the arrangement on the correct leg can also be checked. In the case of a complete body scan, the overlap of several body coils can also be checked. Furthermore, a prediction can be made in step 56 with knowledge of the 3D profile to determine whether the patient touches the inside wall of the tunnel during the measurement. Whether the patient has been given the alarm ball can also be checked. Finally, the profile data of the patient's face in particular can be used to confirm the identity of the patient in order to be able to preclude mistakes.

The method ends in step 57.

As detailed above, this invention enables three-dimensional volume data of the patient under examination, that can be used in many applications, to be determined in a simple manner merely by fitting one further camera.

The invention claimed is:

1. A method for scanning a surface of a patient arranged on a patient's couch of a medical diagnostic device wherein the patient and the couch are moveable, comprising:
    radiating a light beam of a stationary positioning light source onto the patient;
    detecting the light beam on the patient by a stationary image sensor arranged offset relative to the light beam;
    moving the patient relative to the stationary positioning light source so that the light beam passes over a body of the patient; and
    determining a surface of the patient from the detected light beam,
    wherein the medical diagnostic device is a magnetic resonance system with the patient being moved into the system while arranged on the patient's couch, and
    wherein a position and presence of a high-frequency coil of the magnetic resonance system is checked based on the surface of the patient.

2. The method as claimed in claim 1, wherein the positioning light source is arranged in a position that the light beam runs transversely relative to a direction of the movement of the patient.

3. The method as claimed in claim 1, wherein a height profile of the patient relative to the patient's couch is determined along the light beam.

4. The method as claimed in claim 3, wherein the height profile is determined by a light point along the light beam with a real height of the patient having an offset of the light point relative to a zero height of the patient.

5. The method as claimed in claim 1, wherein an orientation of the patient in the diagnostic device is determined from the surface of the patient and a position of the patient's couch and the orientation is compared with an orientation of the patient entered by an operator of the medical diagnostic device.

6. The method as claimed in claim 1, wherein a volume of the patient is estimated from the surface of the patient and a position of the patient's couch and a weight of the patient is estimated from the volume and is compared with a weight input by an operator of the medical diagnostic device.

7. The method as claimed in claim 1, wherein whether the patient touches an inner wall of the diagnostic device is checked based on the surface of the patient.

8. The method as claimed in claim 1, wherein whether the patient has a mobile alarm transmitter is detected based on the surface of the patient.

9. The method as claimed in claim 1, wherein a face of the patient is determined from the surface of the patient and an identity of the patient is confirmed based on the face of the patient.

10. A device for scanning a surface of a patient being arranged on a patient's couch of a medical diagnostic device wherein the patient and the couch are moveable, comprising:
    a stationary positioning light source that beams a light beam onto the patient;
    a stationary image sensor arranged offset relative to the light beam that detects the light beam projected onto the patient;
    a device that moves the patient relative to the stationary positioning light source; and
    a computing unit that calculates a surface pattern of the patient from a position of the light beam detected by the image sensor,
    wherein the medical diagnostic device is a magnetic resonance system with the patient being moved into the system while arranged on the patient's couch, and
    wherein a position and presence of a high-frequency coil of the magnetic resonance system is checked based on the surface pattern of the patient.

11. The device as claimed in claim 10, wherein the patient is arranged on a patient's couch and the device moves the patient by moving the patient's couch.

12. The device as claimed in claim 10, wherein the positioning light source is a laser unit.

13. The device as claimed in claim 10, wherein the positioning light source is arranged in a position that the light beam runs transversely relative to a direction of the movement of the patient.

14. The device as claimed in claim 10, wherein a height profile of the patient relative to the patient's couch is determined along the light beam.

15. The device as claimed in claim 14, wherein the height profile is determined by a light point along the light beam with a real height of the patient having an offset of the light point relative to a zero height of the patient.

16. The device as claimed in claim 10, wherein an orientation of the patient in the diagnostic device is determined from the surface of the patient and a position of the patient's couch and the orientation is compared with an orientation of the patient entered by an operator of the medical diagnostic device.

17. The device as claimed in claim 10, wherein a volume of the patient is estimated from the surface of the patient and a position of the patient's couch and a weight of the patient is estimated from the volume and is compared with a weight input by an operator of the medical diagnostic device.

* * * * *